(12) United States Patent
Sestok, IV

(10) Patent No.: US 10,343,423 B2
(45) Date of Patent: Jul. 9, 2019

(54) IDENTIFICATION OF PAPER MEDIA USING IMPEDANCE ANALYSIS

(71) Applicant: TEXAS INSTRUMENTS INCORPORATED, Dallas, TX (US)

(72) Inventor: Charles Kasimer Sestok, IV, Dallas, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 138 days.

(21) Appl. No.: 15/386,253

(22) Filed: Dec. 21, 2016

(65) Prior Publication Data

US 2017/0254770 A1 Sep. 7, 2017

Related U.S. Application Data

(60) Provisional application No. 62/301,818, filed on Mar. 1, 2016, provisional application No. 62/301,826, filed on Mar. 1, 2016, provisional application No. 62/301,836, filed on Mar. 1, 2016.

(51) Int. Cl.
*B41J 11/00* (2006.01)
*G01N 33/34* (2006.01)

(52) U.S. Cl.
CPC .......... *B41J 11/009* (2013.01); *G01N 33/346* (2013.01)

(58) Field of Classification Search
USPC ........................................ 324/605–611, 71.1
See application file for complete search history.

(56) References Cited

U.S. PATENT DOCUMENTS

| | | | |
|---|---|---|---|
| 4,041,382 A | 8/1977 | Washburn | |
| 5,297,425 A | 3/1994 | Hamby et al. | |
| 8,604,809 B2 | 12/2013 | Eilersen | |
| 2001/0010467 A1 | 8/2001 | Oguma et al. | |
| 2005/0072874 A1* | 4/2005 | Denen | A47K 10/3687 242/563 |
| 2006/0182231 A1 | 8/2006 | Tan et al. | |
| 2007/0268012 A1 | 11/2007 | Kawabata | |
| 2008/0303538 A1 | 12/2008 | Orr | |
| 2008/0303558 A1 | 12/2008 | Orr | |
| 2011/0074392 A1 | 3/2011 | Bartlett et al. | |

(Continued)

OTHER PUBLICATIONS

Chen, Chiouguey J., "Modified Goertzel Algorithm in DTMF Detection Using the TMS320C80," Texas Instruments Application Report, SPRA066, Jun. 1996 (19 pages).

(Continued)

*Primary Examiner* — Vincent Q Nguyen
(74) *Attorney, Agent, or Firm* — Michael A. Davis, Jr.; Charles A. Brill; Frank D. Cimino

(57) ABSTRACT

A microcontroller-based system for identifying a paper type of a sample of paper from a measurement of its electrical impedance. An interdigital dielectric sensor (55) is deployed in the paper path of a printer (PTR), and the electrical impedance at the sensor, as affected by a sheet of paper (P) near the sensor, is measured over a plurality of frequencies of a stimulus signal. The stimulus signal may be sinusoidal or a square wave. The impedance characteristic, in magnitude or phase, or both, is compared against a plurality of reference impedance characteristics, each associated with a paper type, to identify the closest match and thus the type of paper of the sample sheet.

18 Claims, 6 Drawing Sheets

(56) References Cited

U.S. PATENT DOCUMENTS

2011/0115509 A1  5/2011  Kim et al.
2011/0227587 A1  9/2011  Nakanishi et al.
2014/0145729 A1  5/2014  Sobolewski
2016/0077140 A1  3/2016  Todi et al.
2016/0274060 A1  9/2016  Denenberg et al.

OTHER PUBLICATIONS

Mock, Pat, "Add DTMF Generation and Decoding to DSP-uP Designs," Texas Instruments Application Report, SPRA168, copyright 1997 (19 pages).
CDCE(L)913: Flexible Low Power LVCMOS Clock Generator with SSC Support for EMI Reduction, Texas Instruments datasheet dated Jun. 2007, revised Oct. 2016; located at http://www.ti.com/lit.ds.symlink/cdce913.pdf(35 pages).

* cited by examiner

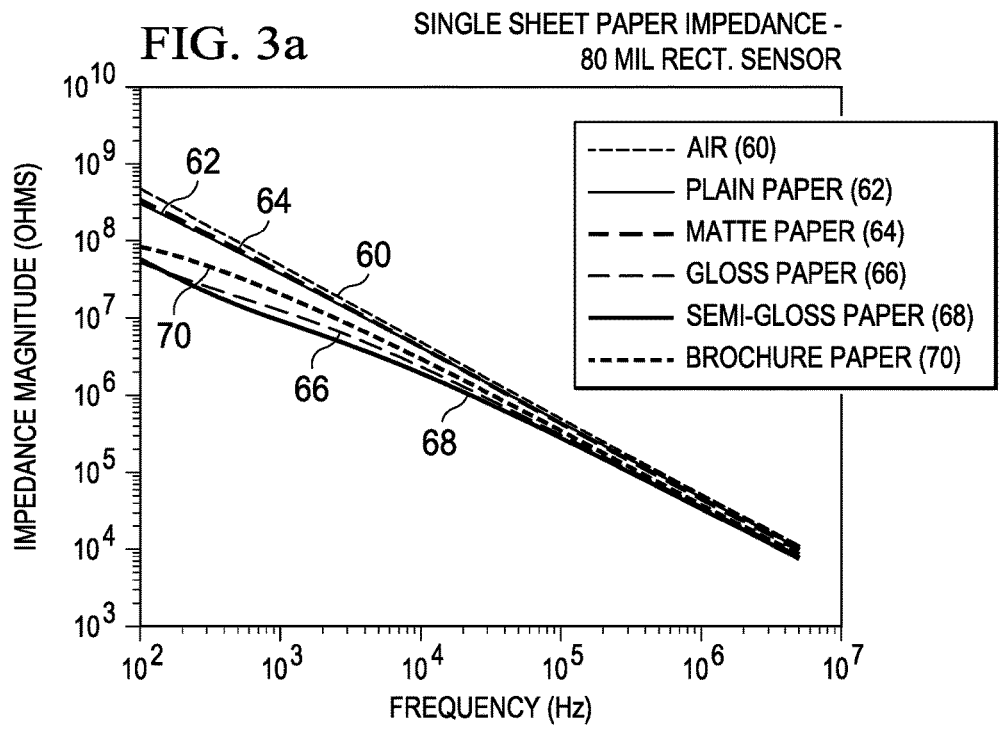
FIG. 3a  SINGLE SHEET PAPER IMPEDANCE - 80 MIL RECT. SENSOR
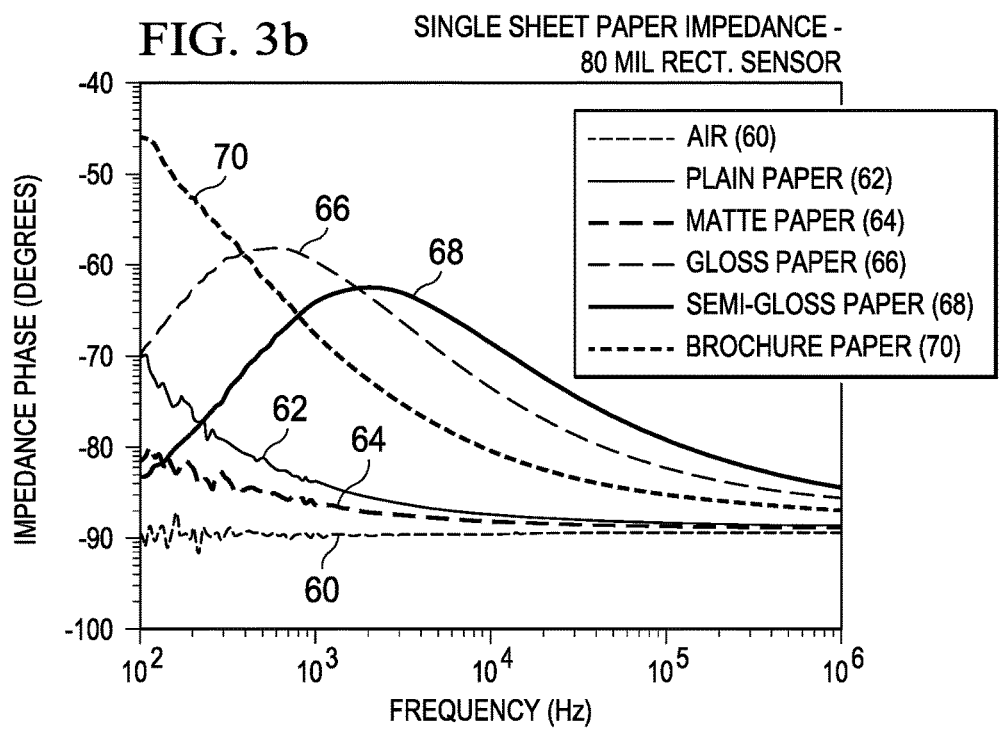
FIG. 3b  SINGLE SHEET PAPER IMPEDANCE - 80 MIL RECT. SENSOR

IDENTIFICATION OF PAPER MEDIA USING IMPEDANCE ANALYSIS

CROSS-REFERENCE TO RELATED APPLICATIONS

This application claims priority, under 35 U.S.C. § 119(e), of Provisional Application Nos. 62/301,818, 62/301,826, and 62/301,836, all three of which were filed Mar. 1, 2016 and incorporated herein by this reference.

STATEMENT REGARDING FEDERALLY SPONSORED RESEARCH OR DEVELOPMENT

Not applicable.

BACKGROUND OF THE INVENTION

This invention is in the field of electronic measurement. Embodiments are more specifically directed to devices and methods of identifying the type and composition of paper media using a measurement of its impedance.

As known in the art, many different types of paper are available for use in conventional desktop and office printer equipment. Ink-jet printers in particular are called upon to print text and images on a wide variety of paper types, ranging from photo paper, to bond paper based on cotton or linen, to paper that is specifically formulated for ink-jet printing, to so-called "plain" paper. For example, photo paper is typically coated with a material that is highly ink-absorbent to provide good color saturation, while preventing wicking of the ink along the fibers of the underlying substrate. Similarly, papers for high quality ink-jet printing will include a similar absorbent coating that prevents wicking or buckling from wetting by large ink loads. Plain paper can support a light link load, but is not suitable for heavier ink usage.

As such, many printers suggest the use of different print settings for the various paper types, in order to attain the highest print quality available for the paper being used. The appropriate setting is typically entered by the user initiating the print task, for example by his selecting of a paper type via a pull-down menu displayed by a computer coupled to the printer. This of course requires attentiveness on the part of the user, as well as knowledge of the type of paper being used as well as the desired print quality. In many cases, it is suspected that the user merely uses the printer default setting, or the last setting entered, in which case the quality of the printed output will be less than optimal if not acceptable, leading to the waste of paper, ink, and time.

BRIEF SUMMARY OF THE INVENTION

Disclosed embodiments provide a low cost sensor system and method of operating the same for detecting the type of paper presently in an input tray.

Disclosed embodiments provide such a sensor that may be realized in a microcontroller for implementation in a desktop printer or similar printing machine.

Disclosed embodiments provide a printer constructed to include such a sensor.

Other objects and advantages of the disclosed embodiments will be apparent to those of ordinary skill in the art having reference to the following specification together with its drawings.

According to certain embodiments, an impedance analyzer function is coupled to a capacitive sensor deployed near a paper feed of the printer. The impedance analyzer includes a stimulus generator for generating a stimulus signal of a fundamental frequency applied to the sensor. The response of the sensor to the stimulus, at each of a plurality of frequencies, is digitized and processed to determine an impedance characteristic over the plurality of frequencies. Processing logic compares the impedance characteristic with a plurality of reference impedance characteristics, each associated with a paper type, to identify the type of paper at the sensor.

BRIEF DESCRIPTION OF THE SEVERAL VIEWS OF THE DRAWING

FIGS. 3a and 3b are plots illustrating variations in impedance magnitude and phase, respectively, over frequency for single sheets of printer paper of various types, as measured by an interdigital dielectric sensor in a system constructed according to an embodiment.

DETAILED DESCRIPTION OF THE INVENTION

The one or more embodiments described in this specification are implemented into a desktop printer of the ink-jet type, as it is contemplated that such implementation is particularly advantageous in that context. However, it is also contemplated that concepts of this invention may be beneficially applied to other applications, for example laser printers and printers using other print technologies, larger scale printers than desktop printers, and also other types of equipment that may receive workpieces of varying composition. Accordingly, it is to be understood that the following description is provided by way of example only, and is not intended to limit the true scope of this invention as claimed.

Figure 1:
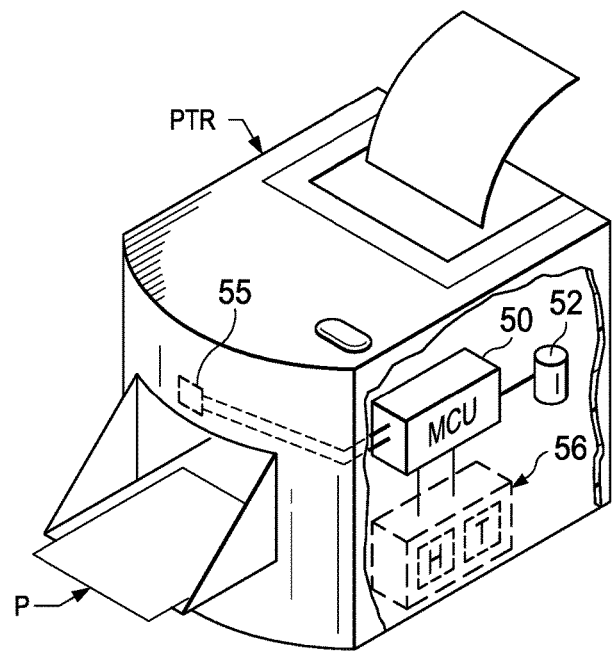
FIG. 1 is an electrical diagram, in block form, of an implementation of embodiments in a desktop application.

FIG. 1 schematically illustrates an implementation of these embodiments in connection with ink-jet printer PTR, by way of example. Printer PTR may be coupled to a computer or computer network in the conventional manner, to receive data corresponding to the text and images to be printed. In this example, paper sample P represents one or more sheets of paper on which the received data are to be printed. Paper sample P may be of any one of a number of paper types, including photo paper, bond paper, plain paper, so-called "ink-jet" paper that is specially formulated or coated for ink-jet printing, card stock of various thicknesses and types, paper suitable for use as brochures, and paper of various finishes such as matte, semi-gloss, and gloss. According to these embodiments, printer PTR includes a system for detecting the type of paper of paper sample P, specifically by measuring the impedance of one or more sheets of the paper when at printer PTR. Based on the results of this detection of paper type, printer PTR can automatically configure its printer settings to optimize the quality of the printed output.

As shown in the example of FIG. 1, this system for detecting paper type includes microcontroller unit (MCU) 50, which is included within the electronics of printer PTR. As known in the art, many modern electronic integrated circuits integrate essentially all necessary functional components of a computer system, whether general purpose or arranged for a particular end application. Those large scale integrated circuits that include the computational capability for controlling and managing a wide range of functions and useful applications are often referred to as a microcontroller, or in some implementations as a "system on a chip", or "SoC", device. Typical modern microcontroller architectures include one or more processor cores that carry out the digital computer functions of retrieving executable instructions from memory, performing arithmetic and logical operations on digital data retrieved from memory, and storing the results of those operations in memory. Other digital, analog, mixed-signal, or even RF functions may also be integrated into the same integrated circuit for acquiring and outputting the data processed by the processor cores.

In this embodiment, microcontroller 50 in printer PTR 50 may be realized by way of such a single-chip microcontroller integrated circuit, in some cases in combination with off-chip circuitry for carrying out the impedance measurements and determinations described in this specification. Microcontroller 50 may be a stand-alone system within printer PTR, separate and distinct from other programmable logic and microcontroller devices that execute the various control functions involved in printer operation, or alternatively may be in whole or in part realized within the programmable logic and microcontrollers that operate printer PTR. It is contemplated that those skilled in the art having reference to this specification will be readily able to realize the circuitry and functions of microcontroller 50 according to these embodiments, as suited for a particular implementation.

In this embodiment, microcontroller 50 is coupled to memory resource 52, which stores a database of a number of reference impedance characteristics for various paper types. Memory resource 52 may reside within printer PTR, indeed within the same integrated circuit as microcontroller 50 if sufficient memory is available, or alternatively may be located outside of printer PTR but otherwise accessible to microcontroller 50 (e.g., over a network connection, etc.).

Microcontroller 50 is also coupled to sensor 55, which in this embodiment is deployed near the paper feed of printer PTR so as to be in contact with or separated by a short distance from one or more sheets of paper sample P. As will be described in further detail below, sensor 55 obtains an electrical measurement of the impedance of paper sample P, from which microcontroller 50 can determine the paper type of that sample P. It may be useful, in many implementations, to sense each single sheet of paper sample P as it feeds into printer P or awaits such feeding, considering that a paper tray or other feed supply may be retaining sheets of multiple paper types in the stack. Alternatively, sensor 55 may be deployed at the paper feed of printer PTR where multiple sheets of paper sample P are retained, such as in a paper tray or the like. In any case, it is desirable that sensor 55 be located in near proximity to the instance of paper sample P for which an impedance is to be obtained, such near proximity including placing sensor 55. Preferably, of course, the paper type of paper sample P is identified prior to printing, in order to optimize the printer settings for carrying out that printing.

According to one embodiment, sensor 55 is an interdigital dielectric sensor. As known in the art, for example as described in Mamishev et al., "Interdigital Sensors and Transducers", *Proc. of the IEEE*, Vol. 92, No. 5 (IEEE, 2004), pp. 808-45, incorporated herein by this reference, interdigital dielectric sensors (also referred to as "fringing field dielectrometry sensors"), are generally constructed as a pair of interdigital comb electrodes at a surface of a circuit board or substrate, where one electrode receiving an excitation or stimulus signal, and the other serving as a sense electrode. Because of the spatial periodicity of the electrodes, the application of the stimulus creates a spatially periodic electric field extending from the surface of the sensor, such that the dielectric properties of the material near that surface affects the impedance of the sensor itself. By virtue of this construction and operation, information regarding the composition of a material placed near the sensor can be acquired by measurement of the impedance of the sensor at multiple frequencies. Interdigital dielectric sensors have the particular advantage of characterizing a material specimen from its surface (i.e., without inserting a probe or otherwise invading the specimen).

Microcontroller 50 may additionally be coupled to environmental sensors 56 as shown in FIG. 1. In this example, environmental sensors 56 include conventional sensors for sensing the relative humidity and ambient temperature of the atmosphere surrounding printer PTR, as it has been observed that humidity, and perhaps temperature, can affect the impedance of paper sample P as sensed by non-invasive sensor 55. Alternatively, additional environmental sensors for sensing other environmental parameters that may affect the impedance measurement may be deployed at printer PTR in the appropriate location. It is contemplated that those of ordinary skill in the art having reference to this specification can readily decide whether to include any environmental sensors 56, or if so, which type, from such information as the effect of temperature, humidity and the like on paper sample P or sensor 55, as well as the necessary resolution in impedance measurement to distinguish paper types from one another.

Figure 2:
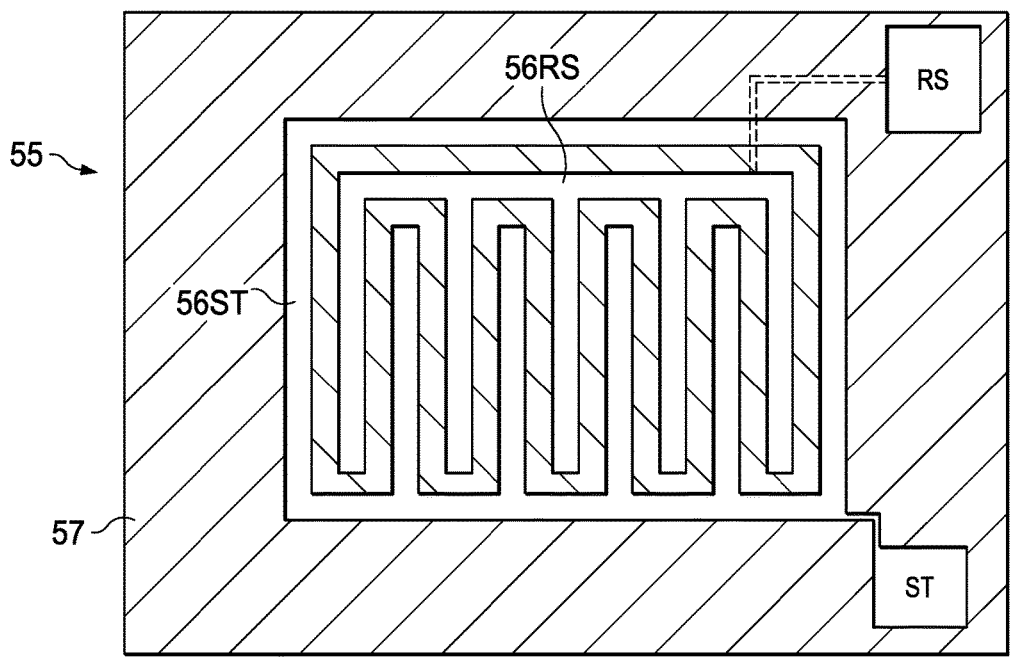
FIG. 2 illustrates, in plan view, an example of an interdigital dielectric sensor as may be used in embodiments.

FIG. 2 generically illustrates an example of sensor 55 according to this embodiment. As shown in the Figure, sensor 55 includes two interdigital comb electrodes 56ST and 56RS disposed at a surface of circuit board 57 or other rigid or flexible member constructed of dielectric material. In an implementation in which sensor 55 is constructed at a two-layer circuit board, a ground plane (not shown) may be formed by metallization on the opposite side of circuit board 57 from electrodes 56ST, 56RS. Alternatively, the ground plane may be an internal metallization layer if sensor 55 is realized in a multiple layer circuit board. In this example, electrode 56ST is connected by a metal trace to terminal pad ST, and electrode 56RS is similarly connected by a metal trace (which is buried at the location crossing under electrode 56ST) to a corresponding terminal pad RS. Connection may be made to terminal pads ST, RS in the conventional manner; in this case, such connection couples these terminal pads to microcontroller 50 as shown in FIG. 1.

As known in the art and as described in the Mamishev et al. article, the spacing between the digits of electrodes 56ST, 56RS determines the range of the sensor. This spacing can range from on the order of 10 mils to on the order of 80 mils, depending on the distance between sensor 55 and paper sheet P in a particular implementation. Electrodes 56ST, 56RS may have a rectangular shape, or may be arranged as concentric alternating rings, as known in the art. Alternatively, non-invasive sensor architectures for measuring the impedance of a specimen from near proximity, other than those of the interdigital dielectric type, are also suitable for use as sensor 55.

It has been discovered, according to this invention, that various types of paper exhibit different electrical impedance characteristics, due to differences in their composition, both in the type of paper pulp or other constitutes of the paper and also from various coatings that are applied to the paper itself. Because the impedance of paper includes a significant reactive component, these differences in impedance appear over frequency, in both of the magnitude and phase components of the impedance spectra for these paper types.

FIG. 7a illustrates variations in impedance magnitude over frequency for single sheets of printer paper of various types, as measured by an interdigital dielectric sensor 55 in a system constructed according to an embodiment. Sensor 55 as used in these measurements was of a rectangular shape, with 80 mil spacing between its surface electrodes in the interdigital region. As evident in FIG. 7a, significant differences in impedance magnitude are present among various groups of paper type, and between these paper types and magnitude spectrum 60 for "air" (i.e., no paper). In particular, spectra 62, 64 for plain and matte paper, respectively, exhibit higher impedance at lower frequencies (e.g., between 100 Hz and 1 kHz) than brochure paper (spectrum 70), and gloss and semi-gloss paper (spectra 68, 70, respectively), and less impedance at these frequencies than air. Similarly, brochure paper exhibits higher impedance than the gloss and semi-gloss samples at these frequencies. Gloss paper can be distinguished from semi-gloss paper, given the gap between spectra 66, 68, which reaches a maximum at around 2 kHz in the example of FIG. 7a. These gaps in the impedance magnitude characteristics as shown in FIG. 7a are contemplated to be greater than the resolution of the impedance measurement system constructed according to many of these embodiments, as will be described in detail below. However, evident from the close resemblance of plain paper (spectrum 62) to matte paper (spectrum 64), certain papers may not be distinguishable only by reference to impedance magnitude characteristics.

FIG. 7b illustrates the phase components of spectra 60 through 70 over the same frequency range as illustrated in FIG. 7a. For the case of the plain and matte paper samples, which would be the most difficult to distinguish based on the magnitude spectra of FIG. 7a, a significant gap in phase behavior between spectra 62 and 64 is evident in FIG. 7b, particularly at frequencies below 1 kHz. As such, the plain and matte paper types can be readily distinguishable from one another, based on the impedance measurements acquired and processed according to these embodiments.

FIG. 7b also illustrates that differences in the shape of the phase characteristic over frequency among paper types provides another way in which these embodiments distinguishes among paper types according to these embodiments. More specifically, phase impedance spectra 62, 64, and 70 all illustrate increasing (more negative) phase angle with frequency, while spectra 66 and 68 exhibit decreasing (less negative) phase with frequency at lower frequencies before then exhibiting increasing phase with frequency. Accordingly, the gloss and semi-gloss paper types can be distinguished from other papers by evaluating whether the phase of impedance increases or decreases with frequency, at frequencies below about 500 Hz in the example of FIG. 7b; in computational terms, the polarity of the first derivative of phase over frequency can be computed from impedance measurements at varying frequency, to distinguish these paper types from one another. Similar computations can be performed to distinguish semi-gloss paper (spectrum 68) from gloss paper (spectrum 66) by determining the local maximum of the phase characteristic, which occurs at about 2 kHz for semi-gloss paper but at about 500 Hz for gloss paper; of course, a significant gap in phase angle is also present between these spectra 66, 68 at lower frequencies, which can be used in making this distinction.

According to these embodiments, data corresponding to a plurality of reference impedance spectra, such as the spectra illustrated in FIGS. 7a and 7b, are stored in a database stored in memory resource 52, and available for access and comparison with newly acquired impedance measurements of paper sample P at printer PTR, as may be executed by microcontroller 50 according to these embodiments. The construction and operation of microcontroller 50 in measuring the impedance exhibited by sensor 55, as affected by a specimen of paper sheet P in near proximity to sensor 55, and the comparison with the library of impedance spectra stored in memory resource 52 so as to identify the paper type of that paper sheet P, will now be described in detail.

Figure 4:
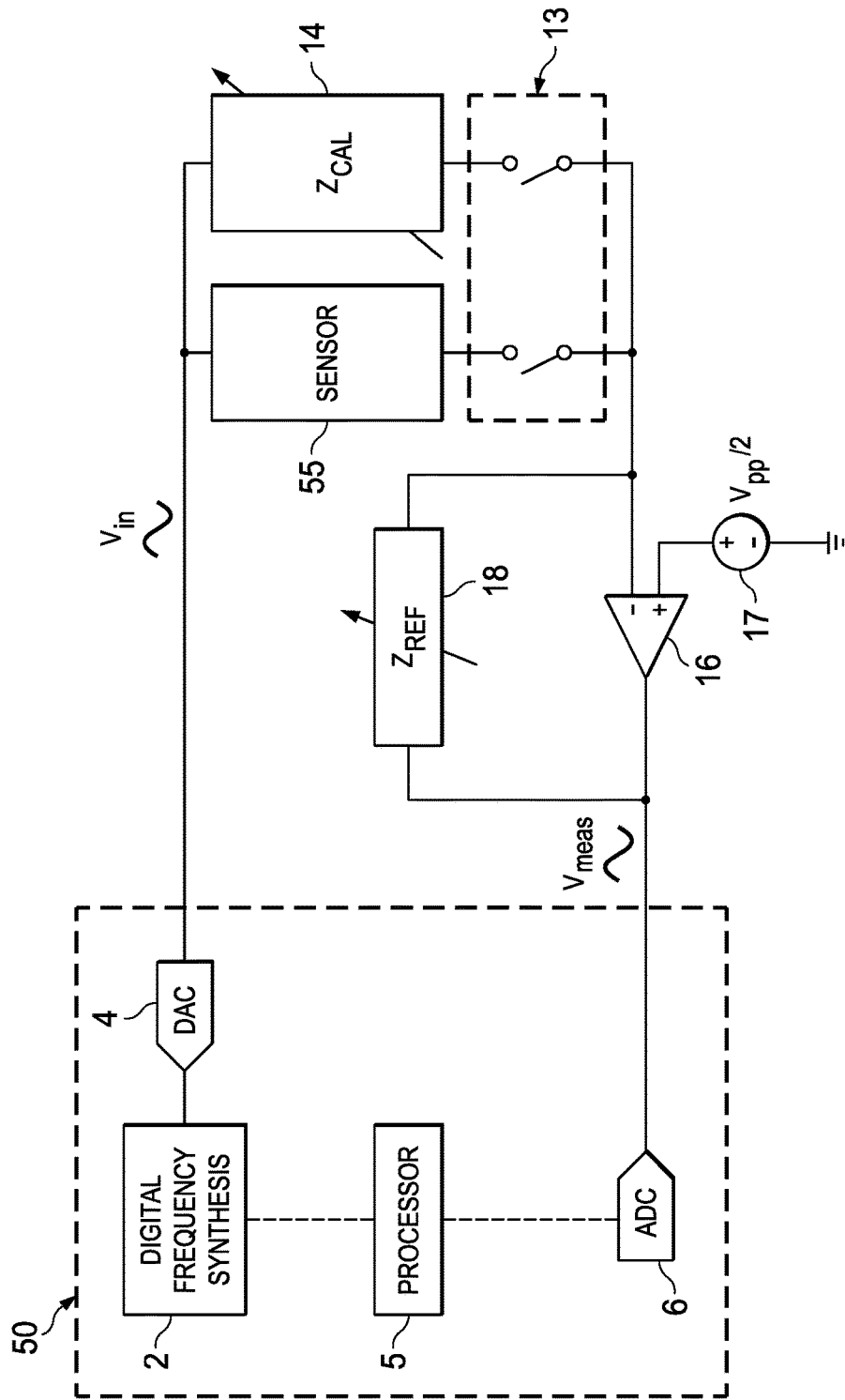
FIG. 4 is an electrical diagram, in block form, of a microcontroller-based sinusoidal stimulus impedance analyzer as may be implemented in a printer according to an embodiment.

Referring now to FIG. 4, the architecture and operation of a microcontroller-based impedance analyzer, as may be implemented by microcontroller 50 in the system of printer PTR shown in FIG. 1, and as may be used in the identification of paper at printer PTR, according to an embodiment will be described. In this example, microcontroller 50 includes digital frequency synthesizer 2, which generates a sample stream corresponding to the desired signal waveform indicated by signals from processor 5. In this example, this sample stream corresponds to a sinusoidal waveform of a selected frequency. The sample stream generated by digital frequency synthesizer 2 is applied to digital-to-analog converter (DAC) 4, which is also realized within microcontroller 10, and which generates the output sinusoidal stimulus $V_{in}$ that will be applied to sensor 55 for measurement of its impedance as may be affected by a nearby paper sample P. As described above, sensor 55 has one terminal receiving stimulus voltage $V_{in}$ (after additional filtering, if desired), and another terminal coupled to the inverting input of operational amplifier 16. Op amp 16 receives a reference voltage, for example at ½ the peak-to-peak amplitude of stimulus voltage $V_{in}$, at its non-inverting input. Reference impedance 18 is connected in negative feedback fashion between the output of op amp 16 and its inverting input. The output voltage $V_{meas}$ from op amp 16 is received by microcontroller 50, and converted to the digital domain by analog-to-digital converter (ADC) 6.

In this inverting amplifier arrangement, the ratio of output voltage $V_{meas}$ to stimulus voltage $V_{in}$ reflects the impedance of sensor 55 relative to the impedance $Z_{REF}$ of reference impedance 18. Op amp 16 maintains a virtual ground at its inverting input, and as such the voltage drop across sensor 55 will be the input voltage $V_{in}$. Additionally, because the input of op amp 16 exhibits a significantly higher impedance than feedback impedance $Z_{REF}$, effectively all of the current conducted through sensor 55 will pass through feedback impedance $Z_{REF}$. Output voltage $V_{meas}$ will thus be proportional to this sensor current conducted through feedback impedance $Z_{REF}$. For example, if the impedance of sensor 55 exactly matches the feedback impedance $Z_{REF}$, output voltage $V_{meas}$ will match stimulus voltage $V_{in}$. Accordingly, the impedance of sensor 55 can be determined from the output voltage $V_{meas}$ presented by op amp 16. As mentioned above, this measurement is performed over frequency, typically by processor 5 controlling digital frequency synthesizer 2 to sweep the frequency of the stimulus voltage $V_{in}$ applied to sensor 55. ADC 6 samples and digitizes output voltage $V_{meas}$ representing the response of sensor 55 to the stimulus at each frequency, and processor 5 analyzes that sample stream, for example via a discrete Fourier transform (DFT), to determine the impedance of sensor 55 at each frequency in the sweep. Both the amplitude and phase of output voltage $V_{meas}$ relative to stimulus voltage $V_{in}$ are considered in quantifying the inductive and capacitive components of the impedance of sensor 55.

In the arrangement of FIG. 4, sensor 55 is connected in parallel with calibration impedance 14, with switches 13 selecting one or the other of these loads. As known in the art, calibration impedance 14 is a known precision impedance that is useful in calibrating the impedance measurement for non-idealities in op amp 16 or presented by the text fixture retaining sensor 55. As suggested in FIG. 5, calibration impedance 14 and may be a variable impedance device (e.g., a bank of selectable precision resistors) to provide accurate calibration over a wide range of impedances. Similarly, reference impedance 18 may also be a variable impedance so as to better match the expected impedance of sensor 55.

While this sinusoidal architecture is capable of analyzing a wide range of load impedances and thus obtain a good measurement of the impedance at sensor 55 and thus the paper type of sample P, the use of a sinusoidal stimulus voltage $V_{in}$ requires the relatively costly circuitry of digital frequency synthesis function 2 and DAC 4, especially if impedance is to be measured at reasonably high precision and at fine resolution. In particular, the number of bits of resolution in the sample stream of the stimulus waveform, as well as the sample rate of that sample stream, translates directly into the complexity of the DAC circuit. As is well known in the art, complex DAC circuits consume significant chip area, and can significantly increase the cost of the microcontroller device. This cost factor can be significant in modern embedded processors and SoC devices, and can limit the sensor applications for which impedance measurements can be performed.

Figure 5:
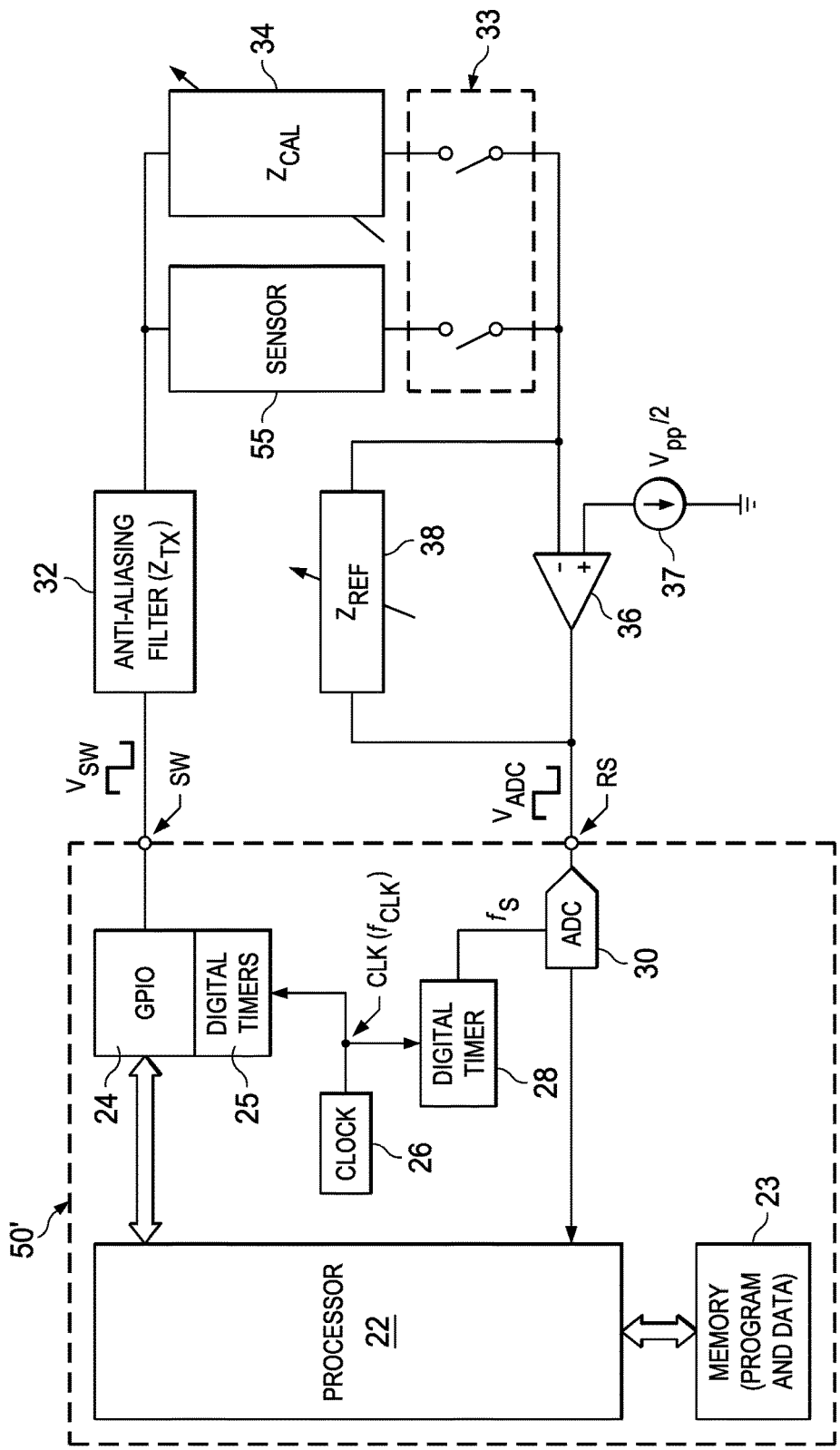
FIG. 5 is an electrical diagram, in block form, of a microcontroller-based square wave stimulus impedance analyzer according to certain embodiments.

FIG. 5 illustrates a microcontroller-based impedance analyzer constructed according to another embodiment, in which a square wave stimulus is applied to sensor 55, thus avoiding the costly circuitry involved in generating the sinusoidal stimulus as shown in FIG. 4. In this implementation, microcontroller 50' includes the appropriate functional circuitry for generating a stimulus waveform to be applied to a device under test, and for analyzing the response of that device to the stimulus in order to determine its electrical impedance. In this regard, microcontroller 50' includes one or more processors 22 (also referred to as "processor cores") that are capable of executing program instructions for carrying out the operations described in this specification. Memory resource 23 in FIG. 5 represents the memory capacity of microcontroller 50', and as such may include memory blocks of various types, including non-volatile memory (e.g., "flash" or other electrically programmable memory) storing program instructions and configuration data for processor 22 and other functions in microcontroller 50', and also volatile (e.g., dynamic or static RAM) memory for storing data involved in those operations. Some of memory resource 23 may be embedded within processors 22 themselves. Examples of microcontroller devices that are suitable for implementation as microcontroller 50' according to these embodiments include the MSP and C2000x families of microcontrollers available from Texas Instruments Incorporated.

In this embodiment, microcontroller 50' includes general purpose input/output (GPIO) function 24, which is coupled to a terminal SW of microcontroller 50'. GPIO 24 includes both input circuitry for receiving and forwarding a digital logic level terminal SW, and driver circuitry for driving a digital voltage level at terminal SW. As typical in the art, GPIO 24 is configured and operates under program control, as executed by processor 22. In this example, the digital logic levels driven at terminal SW by GPIO 24 in its form as an output are constituted by a power supply voltage $V_{pp}$ and ground ($V_{ss}$, or 0 volts). Of course, other digital output voltage levels may alternatively be output from GPIO 24, depending on the construction of the driver circuitry. In this embodiment, GPIO 24 is so configured and operates to drive a square wave signal $V_{SW}$ at these two levels ($V_{pp}$, $V_{ss}$) that will serve as the stimulus applied to sensor 55 to measure its electrical impedance, as may be affected by paper sample P.

Processor 22 is also coupled to analog-to-digital converter (ADC) 30, which is in turn coupled (via conventional "analog front end" circuitry, not shown) to a terminal RS of microcontroller 50'. ADC 30 operates to periodically sample and digitize the voltage at its terminal RS, producing a sample stream that is forwarded to processor 22. According to these embodiments, the voltage sampled by ADC 30 represents the response of sensor 55 to the stimulus of square wave signal $V_{SW}$ applied from GPIO 24. Processor 22 in turn executes the appropriate program instructions, for example as stored in memory resource 23, to determine an impedance measurement for sensor 55 from those sampled voltages. According to these embodiments and as will be described in further detail below, processor 22 will determine that impedance measurement by performing a discrete Fourier transform (DFT) on the sample stream acquired by ADC 30 from the response of sensor 55 to the applied stimulus.

As evident from this description, the stimulus applied to sensor 55 for the impedance measurement is not a sinusoid as in the conventional architecture of FIG. 1, but rather is a square wave signal $V_{SW}$ as generated by GPIO 24. Those skilled in the art will recognize that the use of a square wave will contain frequency components other than the single frequency of a sinusoid, which in this context will complicate the measurement of the electrical impedance of sensor 55. According to these embodiments, however, the generation of the square wave stimulus and the timing of the sampling of the response are based on the same clock signal at a relationship that accounts for lower harmonics of the fundamental square wave stimulus frequency.

Referring to FIG. 5, clock generator circuitry 26 of microcontroller 50' generates a relatively high-speed base clock signal CLK, at frequency $f_{CLK}$, on which both the square wave stimulus $V_{SW}$ and the sampling frequency $f_{ADC}$ applied by ADC 30 are based. In these embodiments, base clock frequency $f_{CLK}$ will be at a higher frequency than either the square wave stimulus frequency $f_{SW}$ or the sampling frequency $f_{ADC}$. As such, the stimulus and sampling frequencies can be generated within microcontroller 50' by relatively simple frequency divider functions, without requiring expensive and complex circuitry such as fractional phase-locked loops and the like as conventionally used to generate sinusoids at specific frequencies. On the stimulus side, base clock signal CLK is applied to digital timers 25 associated with GPIO 24, which divide down the frequency $f_{CLK}$ by an integer divisor to derive the timing of the square wave stimulus. For example, digital timers 25 may include a digital counter that issues a control signal to GPIO 24 to begin a cycle of the square wave (e.g., issue a rising edge) upon the elapsing of a specified number of cycles of clock signal CLK. A second digital counter may also be included within digital timers 25 to define the duty cycle of the square wave stimulus, for example by controlling GPIO 24 to end a pulse (e.g., issue a rising edge) upon the elapsing of a specified number of cycles of clock signal CLK. As such, both the period of the square wave stimulus and its duty cycle are derived as an integer number of cycles of clock signal CLK, according to this embodiment.

Similarly, digital timer 28 is provided in microcontroller 50' to control the sampling frequency $f_{ADC}$ at which ADC 30 samples the response voltage at its corresponding terminal. In this embodiment, digital timer 28 controls ADC 30 to sample and digitize the response voltage upon the elapsing of a specified number of cycles of base clock signal CLK. As such, sampling frequency $f_{ADC}$ is divided down, by a selected integer divisor value, from the frequency $f_{CLK}$ of base clock signal CLK. The relationship of this integer value that defines sampling frequency $f_{ADC}$ and the integer value that defines square wave stimulus frequency $f_{SW}$ according to these embodiments will be described in further detail below.

In the architecture of FIG. 5, terminal SW driven by GPIO 24 is coupled to anti-aliasing filter 32, which is constructed to attenuate higher harmonics of the fundamental frequency of square wave stimulus $V_{SW}$. Filter 32 may be a conventional off-chip (i.e., outside of microcontroller 50') analog low-pass filter of the desired frequency response. For example, filter 32 may be constructed as a conventional $4^{th}$ order multiple feedback low-pass filter, or alternatively as any one of a number of filter architectures and topologies to attain the desired characteristic. Anti-aliasing filter 32 may alternatively be constructed as a band-pass frequency selective frequency filter, rather than a low-pass filter, if desired. If desired, anti-aliasing filter 32 may have a gain less than 1 in order to reduce the peak-to-peak voltage swing of the square wave stimulus as applied to sensor 55, to prevent signal saturation. In any case, anti-aliasing filter 32 is provided to minimize the effect of higher harmonics of the square wave stimulus, so that these harmonics do not significantly contaminate the measured response of sensor 55 at the fundamental frequency of that stimulus waveform.

Sensor 55 is connected at the other side of anti-aliasing filter 32 from GPIO 24 to receive the filtered square wave stimulus $V_{SW}$. In this embodiment, sensor 55 is connected in parallel with variable calibration impedance 34, with switching multiplexer 33 provided in series with these loads 34, 35 to select one or the other for inclusion in the measurement circuit. It is contemplated that switching multiplexer 33 will be controlled by processor 22 or other control circuitry in the system to switch in calibration impedance 34 and switch out sensor 55 when performing calibration of the measurement system, and to switch out calibration impedance 34 and switch in sensor 55 for the impedance measurement. The calibration operation of the architecture of FIG. 5 will be described in further detail below.

An inverting amplifier circuit receives and amplifies the response of sensor 55 to the stimulus from GPIO 24 according to this embodiment. As shown in FIG. 5, sensor 55 (or calibration impedance 34, as the case may be) is applied to a inverting input of differential operational amplifier 36. The non-inverting input of op amp 36 receives a DC voltage equal to the expected DC voltage of the square wave signal; in this example, voltage source 37 applies a voltage of one-half the peak-to-peak amplitude of the square wave stimulus $V_{SW}$, for example one-half the supply voltage ($V_{pp}/2$). The output of op amp 36 is coupled to terminal RS of microcontroller 50', and thus to ADC 30 (via front end circuitry within microcontroller 50', not shown). Reference impedance 38 is connected between the output and the inverting input of op amp 36, in the well-known negative feedback manner. Reference impedance 38 is preferably a precision resistor or variable impedance (e.g., a bank of precision resistors in combination with switches for selectably switching one or more of the resistors into the circuit), and thus has a known impedance for purposes of this impedance measurement.

In measuring the impedance of sensor 55, the inverting amplifier arrangement of op amp 36 and reference impedance 38 will result in the negative feedback current conducted through reference impedance 38 being equal to the current conducted by sensor 55, under the ideal op amp assumption that the inverting input of op amp 36 is at a virtual ground and presents infinite input impedance. Measurement of the response voltage $V_{ADC}$ at terminal RS will thus provide a measure of the current through reference impedance 38 because its impedance $Z_{REF}$ is known. Because the amplitude $V_{SQ}$ is also known (e.g., at supply voltage $V_{pp}$) the response voltage $V_{ADC}$ provides a measure of the impedance $Z_{DUT}$ of sensor 55. More specifically, an estimate $\hat{Z}_{DUT}(f)$ of the impedance of sensor 55 at frequency f can be determined by the architecture of FIG. 5 as:

$$\hat{Z}_{DUT}(f) \approx Z_{REF}\left(\frac{V_{SW}(f)}{V_{ADC}(f)}\right) - Z_{TX}$$

where $Z_{TX}$ is an estimate or measurement of the impedance of anti-aliasing filter 32.

As mentioned above, calibration impedance 34 is connected in parallel with sensor 55, in the signal path between anti-aliasing filter 32 and op amp 36; switching multiplexer 33 operates to switch in either sensor 55 or calibration impedance 34, under the control of processor 22. Calibration impedance 34 may be realized as a resistor or other impedance element with a known impedance value $Z_{CAL}$ measured to the desired precision. As suggested by FIG. 5, calibration impedance 34 may be a variable impedance, for example realized by multiple precision resistors of varying resistance values that may be selectably switched in and out of the circuit, to perform accurate calibration over a wide range of potential sensor impedances.

In general, calibration of the impedance analyzer of FIG. 5 is performed by operating the circuit to measure the impedance of calibration impedance 34 at one or more frequencies, and comparing the measured impedance with the known impedance value $Z_{CAL}$. The manner in which calibration impedance 34 is measured will follow the same approach as described below in connection with FIG. 6 et seq. Differences between the measured impedance value $Z_{CAL}$ and the known impedance of calibration impedance 34 may arise because of non-idealities in op amp 36, variations in the transfer function of anti-aliasing filter 32 from the ideal, inaccuracy in the impedance value of reference impedance 38, and parasitic impedances throughout the circuit, for example at the fixture in which sensor 55 will be inserted for measurement. These differences between the measured and known calibration impedance values $Z_{CAL}$ over frequency may then be used to adjust the corresponding impedance measurements obtained for sensor 55 at those frequencies, in the conventional manner.

Figure 6:
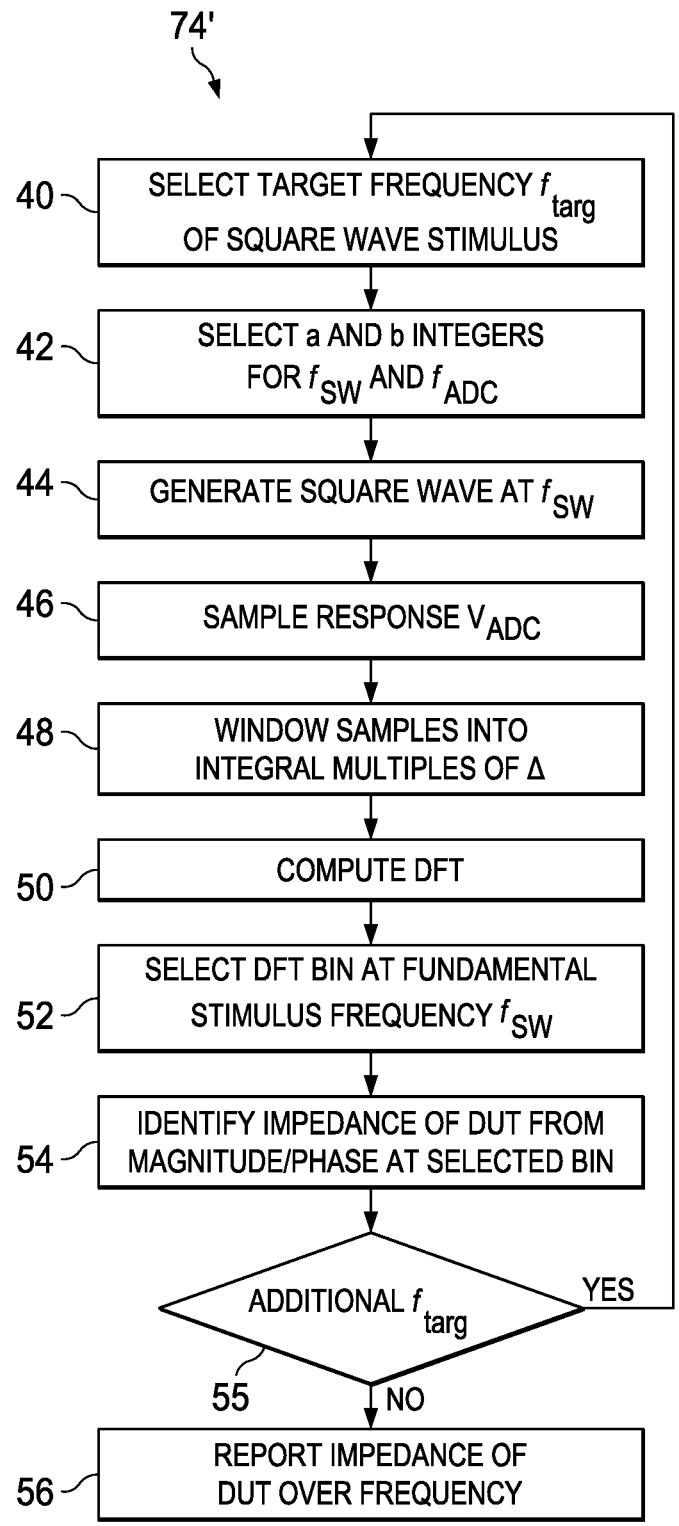
FIG. 6 is a flow diagram illustrating a method of measuring impedance according to certain embodiments.

Referring now to FIG. 6, the general operation of the microcontroller-based impedance analyzer system of FIG. 5 in measuring and analyzing the impedance of sensor 55 over a range of frequencies will now be described. As discussed above, it is contemplated that the appropriate calibration adjustment values have been previously determined over the desired frequency range and over the expected range of sensor impedances. Also as the process of FIG. 6 begins, sensor 55 will have been inserted or otherwise connected into the system of FIG. 5, and switching multiplexer 33 controlled to switch the fixture containing sensor 55 into the circuit and switch calibration impedance 34 out of the circuit.

In process 40, a target frequency $f_{targ}$ at which measurement of the electrical impedance of sensor 55 is to be made is selected, for example in response to a user input communicated to microcontroller 50', or according to an instruction sequence being executed by processor 2 in which the desired target frequencies are established in advance. This target frequency $f_{targ}$ selected in process 40 is the desired frequency $f_{SW}$ of the square wave stimulus $V_{SW}$ generated by GPIO 24. Stimulus frequency $f_{SW}$ is generated by dividing down the frequency $f_{CLK}$ of base clock signal CLK by frequency divisor integer a, such that:

$$T_{SW} = a \cdot T_{CLK}$$

where $T_{SW}$ and $T_{CLK}$ are the periods of the stimulus frequency $f_{SW}$ and the base clock frequency $f_{CLK}$, respectively. Similarly, the sampling rate $f_{ADC}$ of ADC 30 is also divided down from the base clock frequency $f_{CLK}$, by frequency divisor integer b:

$$T_{ADC} = b \cdot T_{CLK}$$

where $T_{ADC}$ is the sampling period at ADC 30. In process 42 according to these embodiments, the frequency divisor integers a and b are selected to produce the desired square wave stimulus frequency $f_{SW}$ and desired sampling rate $f_{ADC}$ at a relationship that reduces interference from aliased harmonics with the fundamental frequency of the response of sensor 55 to that stimulus.

Figure 7:
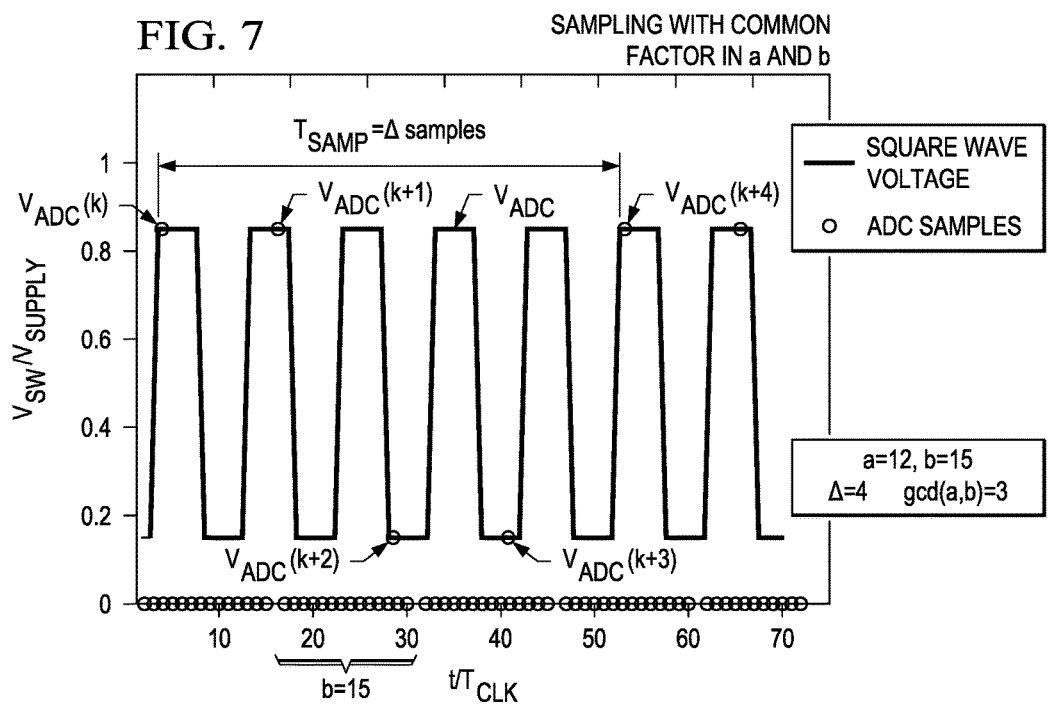
FIG. 7 is a time-based plot illustrating the selection of sampling frequency in the method of FIGS. 2 and 3 according to an embodiment.

FIG. 7 illustrates a simplified example of the relationship between frequency divisor integers a and b relative to the timing of response waveform $V_{ADC}$ appearing at terminal RS, from op amp 36. Because the fundamental frequency of the response $V_{ADC}$ will not be shifted from that of stimulus $V_{SW}$, the period of the response waveform $V_{ADC}$ is equal to the period $T_{SW}$ of stimulus waveform $V_{SW}$ and the response $V_{ADC}$. In the example of FIG. 7, frequency divisor a has the value 12, and frequency divisor b has the value 15. As such, the stimulus period $T_{SW}$ is twelve cycles of base clock signal CLK, and the sampling period $T_{ADC}$ is fifteen cycles of base clock signal CLK. In this example, a sample $V_{ADC}(k)$ is acquired by ADC 30 at a point in time coinciding with a rising edge of response waveform $V_{ADC}$, and the next three samples $V_{ADC}(k+1)$, $V_{ADC}(k+2)$, and $V_{ADC}(k+3)$ are acquired at points in time corresponding to different phases of response waveform $V_{ADC}$. In this example, the relationship of integers a and b (and thus the relationship between the stimulus period $T_{SW} = a \cdot T_{CLK}$ and the sampling period $T_{ADC} = b \cdot T_{CLK}$) results in the fourth sample $V_{ADC}(k+4)$ being acquired coincident with the rising edge of response waveform $V_{ADC}$. One can derive a separation number $\Delta$ corresponding to the number of samples $V_{ADC}(n)$ acquired by ADC 30 at distinct phases of the response waveform $V_{ADC}$ as:

$$\Delta = \frac{a}{gcd(a, b)}$$

where gcd(a, b) is the greatest common divisor of integers a, b. In the example of FIG. 7, the greatest common divisor of a=12 and b=15 is gcd(a,b)=3. Accordingly, samples $V_{ADC}(n)$ are acquired at the same phase of response signal $V_{ADC}$ every $\Delta$=4 samples, which is represented in FIG. 7 as the period $T_{samp} = \Delta \cdot T_{ADC} = 4 \, T_{ADC}$.

This separation number $\Delta$, which corresponds to the density of distinct phases of the stimulus waveform $V_{SW}$ that are sampled by ADC 30, provides an indication of the resolution of the measured response $V_{ADC}$. In an undersampled situation such as that shown in FIG. 7, and assuming that the sampled waveform is periodic and stable, one can reconstruct the waveform at high resolution by reordering samples acquired at different phases of the waveform over a number of cycles. In the case shown in FIG. 7, the separation $\Delta$=4 results in only distinct phases being sampled, regardless of the number of cycles. From the standpoint of resolution and precision, it is therefore useful for the separation number $\Delta$ to be as large as possible. Because the separation number $\Delta$ is inversely proportional to the greatest common divisor of frequency divisor integers a and b, the largest separation number $\Delta$ of samples for a given value of frequency divisor a, will be obtained by selecting integers a and b in process 42 to be relatively prime.

According to these embodiments, additional constraints due to limitations in the circuitry in microcontroller 50' are also considered in selection of frequency divisor integers a and b in process 42. One such constraint is the maximum sampling frequency of ADC 30. It is contemplated that this maximum sampling frequency may be relatively low, especially for microcontroller-based implementations in which ADC 30 is relatively low performance to reduce device cost. Because measurement accuracy is improved at higher sampling rates, it is optimal for integer b to be selected so that the sampling frequency $f_{ADC}$ is as close to the maximum available frequency as possible. For example, if the frequency $f_{CLK}$ of clock signal CLK is 48 MHz and the maximum sampling frequency $f_{ADC}$ is 1 MHz, the value of frequency divisor integer b selected in process 42 is at least 48, preferably as close to 48 as possible to obtain the highest possible sampling resolution.

As mentioned above and as will be described in further detail below, processor 22 will operate to determine the impedance of sensor 55 by executing a discrete Fourier transform (DFT) on the sample stream of response voltage $V_{ADC}$ acquired by ADC 30. Those skilled in the art will recognize that the DFT of a sample stream involves the "windowing" of the sample stream into a number of samples that are considered as the signal values within one period of a periodic sampled signal of infinite duration. While large numbers of samples within a DFT window are preferred, the available memory, computational capacity for the DFT operation, and time required to make a measurement typically constrain the maximum DFT window length.

In addition, it has been discovered, according to these embodiments, that the selection in process 42 of the frequency divisor integer values a and b is important in reducing the interference from aliased harmonics with the fundamental frequency of the response voltage $V_{ADC}$. This is accomplished, according to these embodiments, by selecting frequency divisor integers a, b so that the number of samples N in a DFT window is an integer multiple of the separation number Δ of samples acquired at distinct phases of the response waveform acquired by ADC 30. Referring to FIG. 7, it is evident that the period $T_{samp}$ of Δ samples corresponds to an integer number of cycles of the stimulus (and response) waveform. By selecting the window length N to be an integer multiple of the separation number Δ (i.e., N=qΔ, for some integer q), and because a group of Δ samples itself represents an integer number of periods $T_{SW}$, the DFT window of length N will cover an integer number of periods $T_{SW}$. Lower order aliased harmonics of the fundamental frequency will tend to fall into different DFT bins from the fundamental DFT bin, which is the bin of importance for determining the impedance of sensor 55. Conversely, the strongest aliased harmonic affecting the fundamental frequency bin can be a higher order harmonic, preferably at a frequency that can be attenuated by anti-aliasing filter 32. In many cases, it has been observed that the effect of these higher order aliased harmonics on the DFT analysis of the impedance can be held below the white noise floor of the system, which allows ADC 30 to under-sample response voltage $V_{ADC}$.

It has further been observed, according to these embodiments, that the value of the separation number Δ of samples acquired by ADC 30 at distinct phases of the response waveform can affect the level of aliased harmonic noise on the response signal at the fundamental frequency. In a general sense, the interference resulting from these aliased harmonics appears as a set of equally spaced tones near the fundamental frequency. But it has been observed that odd-numbered values of the separation number Δ results in this interference appearing as a series of equally-spaced tones with alternating positive and negative amplitudes. Similarly, even-numbered values of the separation number Δ that are not divisible by four also results in interference in the form of a series of equally-spaced tones with alternating positive and negative amplitudes, but with a greater net amplitude than in the odd-valued Δ case. In contrast, values of the separation number Δ that are divisible by four result in the interference series having tones on the low side of the fundamental frequency that all have the same polarity amplitude (e.g., negative amplitude) and tones on the high side that all have the same polarity amplitude (e.g., positive amplitude), amounting to an overall higher level of aliased harmonic interference with the response signal at the fundamental frequency.

According to this embodiment, therefore, a low-cost implementation of an impedance analyzer can be readily attained. More specifically, this embodiment allows a digital output from an integrated circuit, such as a GPIO function in a microcontroller, to generate the stimulus for the measurement of an impedance over a range of frequencies, thus eliminating the need for costly and area-intensive circuits such as fractional PLLs and high-precision DACs as conventionally used to generate sinusoids. In addition, this embodiment allow relatively low performance analog-to-digital converters (ADCs) to sample the impedance response, indeed under-sampling the response at higher stimulus frequencies, without resulting in significant interference from aliased harmonics. It is therefore contemplated that impedance analyzer functions according to this embodiment can be deployed into an application such as the identification of paper type described in this specification.

Figure 8:
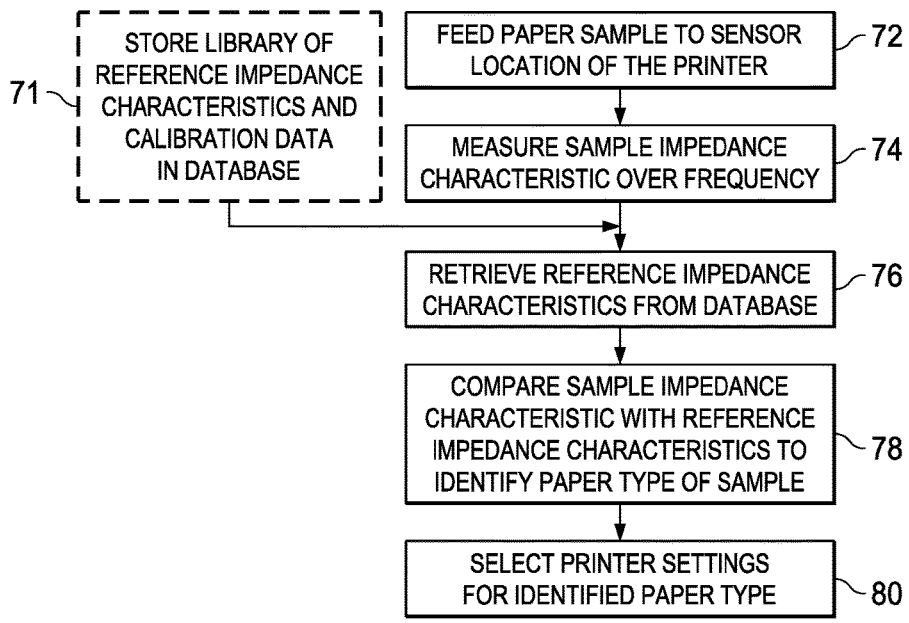
FIG. 8 is a flow diagram illustrating the operation of a printer according to an embodiment.

Referring now to FIG. 8, a process for identifying the paper type of an instance of one or more sheets of paper from a measurement of its impedance, as may be performed at a desktop or other type of printing equipment, will be described in connection with various embodiments. By way of example, this description will refer to the system described above in connection with FIG. 5 and realized at printer PTR in the manner shown in FIG. 5, in which a square wave stimulus is generated and the response processed by microcontroller 50', in combination with sensor 55.

The identification of the paper type of paper sample P at printer PTR begins with the storing of reference impedance characteristics for various paper types in memory resource 52. These data may be stored in the form of a database or other arrangement of data as suitable for the computations to be performed by processor 22. In addition, if one or more environmental sensors 56 are deployed at printer PTR and accessed by MCU 20, the data stored in memory resource 52 may also include calibration data by way of which processor 22 can adjust the impedance measurements for humidity and other environmental factors. It is contemplated that the reference impedance characteristics, and calibration data, if any, will be obtained in advance by characterization and observation, and thus pre-stored in memory resource 52 prior to the identification process. For example, these reference impedance characteristics may be determined by the printer manufacturer and pre-installed into printer PTR at the time of its manufacture. In the system of FIG. 5, memory resource 52 may correspond to on-chip memory 23 realized within MCU 20; alternatively, memory resource 52 may be external memory within printer PTR that is available to MCU 20.

The measurement of an instance of paper sample P itself begins with the feeding of one or more sheets of the paper to the location of sensor 55 in printer PTR, in process 72. While the location of sensor 55 may vary, as described above, it is desirable for the measurement to occur somewhere in the feed path, either at the paper tray or supply, or along the path that each sheet travels in the printing process.

In this regard, it has been observed that the measured impedance will vary for varying numbers of sheets, up to a number of sheets at which the impedance saturates. For example, for sensor 55 of a rectangular pattern with 80 mil spacing between electrodes being used to sense the impedance of plain paper, the sensed impedance value varies with the number of sheets in the paper stack up to about ten sheets, beyond which the measured impedance saturates. It is contemplated that this saturation threshold corresponds to the depth to which the electric field extends in paper sample P, which is dependent on the electrode spacing of sensor 55 as known in the art. For best performance, the number of paper sheets at the location of sensor 55 should be either a single sheet or beyond the saturation threshold. For the case of desktop printers, in which different types of paper may be supplied by different paper trays, or in which different paper types may be stacked within the same paper tray, it is expected that sensing of a single sheet will provide the best results, in which case process 72 will be performed by feeding a single sheet along the feed path to the location of sensor 55.

In process 74, the impedance exhibited by paper sample P is measured by microcontroller 50' over frequency, for example according to the process described above relative to FIG. 6. As noted above, sensor 55 in near proximity to paper sample P will correspond to the "DUT" in that measurement process, such that the impedance that is measured reflects the properties of paper sample P under current conditions, over a frequency range of interest for the expected paper types. The impedance values determined in process 74 may be calibrated with humidity and other environmental parameters, for example as measured by environmental sensors 56 described above (and according to the calibration data stored in memory resource 52). As a result of process 74, data corresponding to the impedance characteristic over frequency for paper sample P are acquired. In process 76, microcontroller 50' retrieves the relevant reference impedance characteristic data from the database stored in memory resource 52.

In process 78, processor 22 in microcontroller 50' compares the sample impedance characteristic acquired in process 74 with the reference impedance characteristics retrieved from memory resource 52 in process 76, to identify the reference impedance characteristic to which the sample impedance data most closely resembles. It is contemplated that this comparison may be performed according to any one or more of a wide variety of classification algorithms and techniques. In each case, it is contemplated that this comparison will be performed by processor 22 or other processor logic in microcontroller 50' executing a sequence of program instructions, for example as stored in memory 23 of microcontroller 50'.

According to one approach, comparison process 76 may be performed by processor 22 executing a software routine in which some type of statistical comparison process is used to identify one of the reference impedance characteristics that is the closest fit to the impedance characteristic acquired for paper sample P in process 74, for example by way of a least squared error or other closeness statistic.

According to another approach, process 76 may be performed by comparing the impedance magnitude and phase angle values at specific frequencies for paper sample P with those of the reference impedance characteristics retrieved from memory resource 52. The particular frequencies at which these values are compared may be those values at which the largest "gaps" between reference impedance characteristics are exhibited, ensuring that the resolution of the measurement is relatively small against those gaps. For example, referring to FIG. 3a, the impedance magnitude for paper sample P at a low frequency, e.g., 100 Hz, may be compared against the reference impedance magnitude values at that frequency to determine whether paper sample P resembles a glossy paper (gloss and semi-gloss) or brochure, on one hand, or a plain type paper (plain or matte) or no paper (air) on the other hand, since the gap between the spectra for those two groups of paper type is largest at that frequency. If paper sample P more resembles a glossy paper, its impedance magnitude at a higher frequency, for example 1 kHz, may then be compared against the reference impedance magnitudes for the gloss, semi-gloss, and brochure paper, since the gaps among spectra 66, 68, 70 are large at that frequency. Similar comparisons may be made for the phase angles. For example, the phase of the impedance for paper sample P at 100 Hz may be compared against that of the reference impedance phases at that frequency, as the gaps among the spectra for groups of papers (brochure paper spectrum 70 vs. gloss paper spectrum 66 and plain paper spectrum 62 vs. matte paper spectrum 64 and semi-gloss paper 68) are quite large at that frequency. The phase angle value for paper sample P at about 500 Hz may be compared with those of the reference impedance characteristics, especially to distinguish semi-gloss paper from matte paper, and gloss paper from plain paper, both of those pairs having similar phase angles at 100 Hz. The particular comparison algorithm employed in process 76 to compare magnitude and phase values at particular frequencies according to this approach will of course depend on the nature of the reference impedance characteristics for the various papers.

Another approach to process 76 takes advantage of the different shape of the phase component of reference impedance characteristics, as illustrated by the spectra of FIG. 3b. As evident in that plot and as described above, some papers (gloss and semi-gloss paper) exhibit a phase characteristic that first becomes less negative with increasing frequency, and then becomes more negative after about 500 Hz and 1200 Hz for spectra 66, 68, respectively. On the other hand, the phase components of spectra 62, 64, and 70 all become more negative with frequency from 100 Hz, until reaching their asymptotic phase angles. Accordingly, process 76 may include a determination of the polarity of the first derivative of phase with frequency, by way of which it can distinguish the gloss and semi-gloss papers from the other papers. Other comparisons, for example of the magnitude and phase at selected frequencies, can then be made to identify the particular reference impedance characteristic within that group to which the sample impedance characteristic most closely matches.

Adaptive networks, or so-called neural networks, are computational approaches (and hardware, in some implementations) that are capable of recognizing patterns by a non-heuristic approach. For example, in a "learning" phase, an adaptive network can be used to evaluate the impedance characteristic over frequency of a number of samples of various types of paper, and to adjust its computations (e.g., weighting factors in a backpropagation-style network) according to the difference between its computed result and the true paper type. Upon a sufficient number of training examples, the adaptive network will be able to identify the reference impedance characteristic closest to that of a new paper sample P with some degree of confidence.

It is contemplated that those skilled in the art having reference to this specification will be readily able to implement any one or more of these and other classification algorithms and techniques as best appropriate for comparing the sample impedance characteristic acquired in process 74 with a closest reference impedance characteristic. Process 76 concludes with the identification of the paper type of that closest reference impedance characteristic, as the paper type of paper sample P.

Once the paper type is identified in process 76, printer PTR can then use that information in its operation. For example, as shown in FIG. 8, printer PTR can select or change its printer settings to optimize its printing for the identified paper type. Alternatively, printer PTR may notify the user of the identified paper type, particularly if the setting changes may be significant from a cost or operational standpoint. Other applications of the paper type information acquired according to these embodiments are also contemplated.

These embodiments provide important advantages in the operation of a printer, particularly ink-jet printers for which the optimization of print quality depends to a significant extent on the type of paper being used. These embodiments provide an efficient and low-cost sensor and identification system that can be readily implemented into small scale printers, such as desktop and home printers, so as to optimize the printed output in a way that minimizes user input and interaction. It is contemplated that both high print quality and also efficiency in ink usage can thus be provided over a wide range of printer applications.

While one or more embodiments have been described in this specification, it is of course contemplated that modifications of, and alternatives to, these embodiments, such modifications and alternatives capable of obtaining one or more the advantages and benefits of this invention, will be apparent to those of ordinary skill in the art having reference to this specification and its drawings. It is contemplated that such modifications and alternatives are within the scope of this invention as subsequently claimed herein.

What is claimed is:

1. A system for identifying a paper type of a paper sample, the system comprising:
    a memory configured to store reference impedance characteristics of paper types;
    stimulus generator circuitry having a stimulus output, the stimulus generator circuitry configured to generate a stimulus at the stimulus output;
    a sensor having: a stimulus component coupled to the stimulus output, the stimulus component configured to generate electric fields through the paper sample at fundamental frequencies responsive to the stimulus; and a sense component configured to sense the electric fields and generate analog signals representative thereof;
    an analog-to-digital converter having: an analog input coupled to the sense component; and a digital output; and
    integrated circuitry coupled to the digital output and the memory, the integrated circuitry configured to: receive digital information from the digital output, the digital information representative of the analog signals; responsive to the digital information, determine a sample impedance characteristic for the paper sample; and compare the sample impedance characteristic with the reference impedance characteristics to identify the paper type of the paper sample.

2. The system of claim 1, wherein the stimulus is a sinusoidal stimulus.

3. The system of claim 1, wherein the stimulus is a square wave stimulus.

4. The system of claim 3, further comprising:
    clock circuitry configured to generate a base clock signal; and
    an anti-aliasing filter, coupled between the stimulus output and the stimulus component, the anti-aliasing filter configured to filter the stimulus to remove frequencies above a threshold;
    the stimulus generator circuitry comprising a digital driver circuit configured to generate the square wave stimulus at a fundamental frequency having a period equal to a first integer number of cycles of the base clock signal;
    the analog-to-digital converter being configured to receive the analog signals at a sample frequency having a period equal to a second integer number of cycles of the base clock signal; and
    the integrated circuitry being configured to execute a discrete Fourier transform on the digital information, using a window of samples numbering an integer multiple of a separation number, the separation number defined by: the first integer, divided by a greatest common divisor of the first and second integers.

5. The system of claim 1, wherein the sensor comprises: an interdigital dielectric sensor.

6. The system of claim 1, wherein the stimulus generator circuitry, the analog-to-digital converter, and the integrated circuitry are integral in a single integrated circuit.

7. The system of claim 1, wherein the sample impedance characteristic comprises:
    a sample magnitude versus frequency characteristic; and
    a sample phase versus frequency characteristic.

8. The system of claim 7, wherein the integrated circuitry is configured to compare the sample impedance characteristic with the reference impedance characteristics by executing operations comprising:
    detecting a polarity of the first derivative of the sample phase versus frequency characteristic over frequency; and
    selecting one or more of the reference impedance characteristics exhibiting a phase versus frequency characteristic with a same polarity of the first derivative over frequency.

9. The system of claim 1, wherein the integrated circuitry is configured to compare the sample impedance characteristic with the reference impedance characteristics by executing operations comprising:
    comparing a value of the sample impedance characteristic at a first frequency with values of at least first and second reference impedance characteristics at the first frequency;
    determining which of the at least first and second reference impedance characteristics most closely matches the sample impedance characteristic at the first frequency; and
    repeating the comparing and determining at a second frequency.

10. The system of claim 1, wherein the integrated circuitry is configured to compare the sample impedance characteristic with the reference impedance characteristics by executing operations comprising:
    applying the sample impedance characteristic to an adaptive network.

11. A method of identifying a paper type of a paper sample, the method comprising:
    placing a paper sample near a sensor;
    applying a stimulus signal at fundamental frequencies to the sensor;
    sampling a response signal from the sensor, in response to the stimulus signal;
    processing the sampled response signal for the fundamental frequencies, to determine a sample impedance characteristic for the paper sample; and
    comparing the sample impedance characteristic with the reference impedance characteristics to identify the paper type of the paper sample.

12. The method of claim 11, wherein the stimulus signal is a sinusoidal stimulus signal.

13. The method of claim 11, wherein the stimulus signal is a square wave stimulus signal.

14. The method of claim 13, further comprising:
    generating a base clock signal; and
    filtering the stimulus signal to remove frequencies above a threshold;
    wherein applying the stimulus signal comprises generating the square wave stimulus signal at a fundamental frequency having a period equal to a first integer number of cycles of the base clock signal;
    wherein sampling the response signal comprises sampling the response signal at a sample frequency having a period equal to a second integer number of cycles of the base clock signal; and
    wherein processing the sampled response signal comprises executing a discrete Fourier transform on the sampled response signal, using a window of samples numbering an integer multiple of a separation number, the separation number defined by: the first integer, divided by a greatest common divisor of the first and second integers.

15. The method of claim 11, wherein the sensor comprises:
an interdigital dielectric sensor.

16. The method of claim 11, wherein the sample impedance characteristic comprises:
a sample magnitude versus frequency characteristic; and
a sample phase versus frequency characteristic.

17. The method of claim 16, wherein comparing the sample impedance characteristic comprises:
detecting a polarity of the first derivative of the sample phase versus frequency characteristic over frequency; and
selecting one or more of the reference impedance characteristics exhibiting a phase versus frequency characteristic with a same polarity of the first derivative over frequency.

18. The method of claim 11, wherein comparing the sample impedance characteristic comprises:
comparing a value of the sample impedance characteristic at a first frequency with values of at least first and second reference impedance characteristics at the first frequency;
determining which of the at least first and second reference impedance characteristics most closely matches the sample impedance characteristic at the first frequency; and
repeating the comparing and determining at a second frequency.

* * * * *